United States Patent [19]

Bain et al.

[11] 4,356,038
[45] Oct. 26, 1982

[54] STABILIZATION OF CHLORINATED ALIPHATIC HYDROCARBONS AND USE OF STABILIZED COMPOSITION IN CLEANING ARTICLES

[75] Inventors: David Bain, Sutton Leach; John E. Martin, Grappenhall; John H. Saul, Upton-by-Chester; Neil Winterton, Tarvin, all of England

[73] Assignee: Imperial Chemical Industries Limited, London, England

[21] Appl. No.: 170,835

[22] Filed: Jul. 16, 1980

[30] Foreign Application Priority Data

Jul. 25, 1979 [GB] United Kingdom ................ 7925867
Apr. 25, 1980 [GB] United Kingdom ................ 8013705

[51] Int. Cl.$^3$ .......................... C11D 7/50; C23G 5/02; C09K 15/16; C07C 17/42
[52] U.S. Cl. .......................................... 134/2; 134/31; 252/171; 252/364; 252/405; 570/110
[58] Field of Search .................. 252/364, 171, 405; 134/11, 2, 31; 570/110

[56] References Cited

U.S. PATENT DOCUMENTS

| | | | |
|---|---|---|---|
| 3,000,978 | 9/1961 | Fredenburg | 570/118 |
| 3,049,571 | 8/1962 | Brown | 570/110 |
| 3,238,065 | 3/1966 | Fullhart, Jr. | 134/11 |
| 3,281,480 | 10/1966 | Hardies | 252/171 X |
| 3,549,715 | 12/1970 | Cormany et al. | 570/110 |
| 4,115,461 | 9/1978 | Spencer et al. | 252/171 X |

FOREIGN PATENT DOCUMENTS

| | | |
|---|---|---|
| 788495 | 6/1968 | Canada. |
| 1435548 | 5/1976 | United Kingdom ................ 252/171 |
| 1439970 | 6/1976 | United Kingdom ................ 252/171 |
| 2024242 | 1/1980 | United Kingdom. |
| 2024243 | 1/1980 | United Kingdom. |

Primary Examiner—Richard D. Lovering
Attorney, Agent, or Firm—Cushman, Darby & Cushman

[57] ABSTRACT

A solvent composition for cleaning metal and other articles which comprises 1,1,1-trichloroethane having dissolved therein a stabilizing amount of a mixture of stabilizing components comprising (i) tertiary butanol (ii) nitromethane and (iii) 1-or 2-nitropropane or nitroethane, in which mixture the specified stabilizing components are present in the mole fraction percent ranges encompassed by Contour K in FIG. 1 of the drawings in the case where component (iii) is 1-or 2-nitropropane or by Contour A in FIG. 2 of the drawing in the case where component (iii) is nitroethane.

13 Claims, 2 Drawing Figures

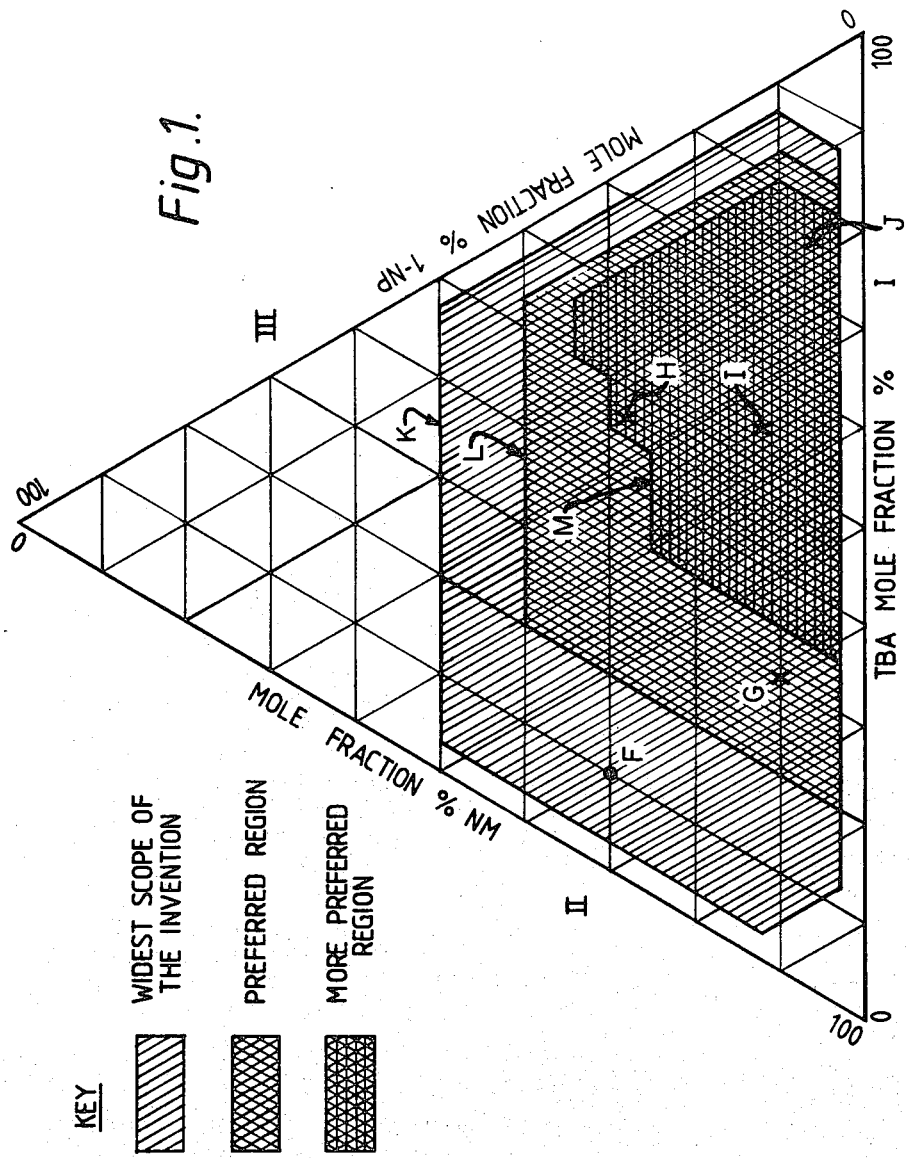

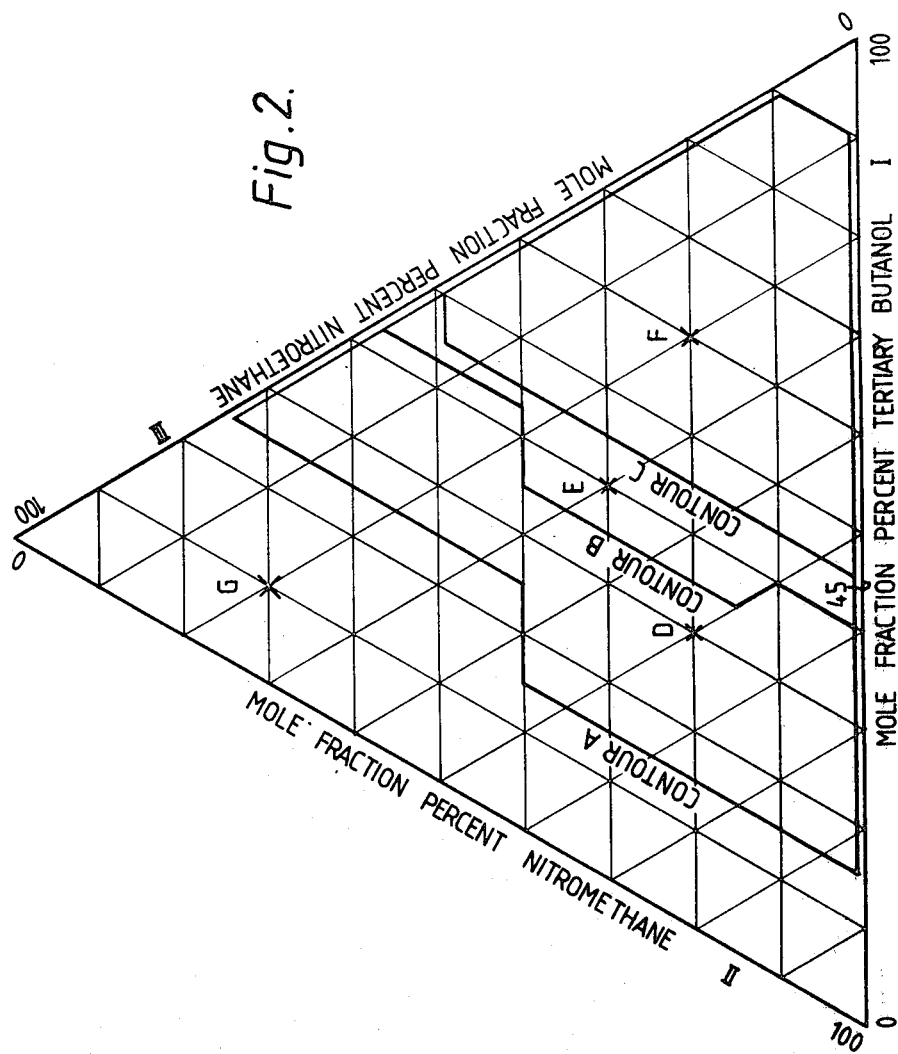

STABILIZATION OF CHLORINATED ALIPHATIC HYDROCARBONS AND USE OF STABILIZED COMPOSITION IN CLEANING ARTICLES

This invention relates to the stabilisation of 1,1,1-trichloroethane.

A wide variety of organic compounds have been proposed for the stabilisation of 1,1,1-trichloroethane. These include, by way of example, ethers e.g. 1,4-dioxane and 1,3-dioxolane, ketones, alkyl nitrates, amines, phenolic compounds, aliphatic alcohols e.g. tertiary butanol, nitroalkanes containing one to three carbon atoms, epoxides e.g. 1,2-butene, and alkyl substituted pyrroles. Hundreds of different mixtures of stabilisers from these and other groups of compounds have been proposed.

We have now found that a surprising and improved effect is obtained in the stabilisation of 1,1,1-trichloroethane by incorporating in the solvent (i) tertiary butanol, (ii) nitro-methane and (iii) 1- or 2-nitropropane or nitroethane. Mixtures of 1-nitropropane and/or 2-nitropropane and nitroethane may be used.

We have found, surprisingly, that by adding specific molar proportions of said nitroalkanes and tertiary butanol to 1,1,1-trichloroethane, the stability of the solvent is significantly greater than that conferred on the solvent by adding the same total molar concentration of any one of said nitroalkanes alone, any mixture of said nitroalkanes, or tertiary butanol. By incorporating all three of the stabilising components (i) (ii) and (iii) in the solvent, a synergistic or interelated stabilising effect is obtained which is entirely unexpected.

The molar proportions of the three stabilising components, namely tertiary butanol, nitromethane and nitropropane or nitroethane which are within the scope of the present invention are illustrated in the triangular diagrams shown in the drawings accompanying the specification.

BRIEF DESCRIPTION OF DRAWINGS

FIG. 1 relates to a stabilizer mixture using nitropropane as component (iii).

FIG. 2 relates to a mixture containing nitroethane as component (iii).

Referring to FIG. 1 of the drawings, the lines I,II and III of the triangular diagram represent the mole fraction percent of each of the three components (I) t-butanol, (II) nitromethane and (III) nitropropane (the nitropropane illustrated is 1-nitropropane). Contour K encompasses an area representing the broadest range of the mole fraction percent of the three components which are within the scope of the invention. Contour L encompasses an area representing a preferred range of mole fractions percent of the three components. Contour M encompasses an area representing an especially preferred range of mole fractions percent of the three components.

The ranges represented by the Contours are given for convenience in Table I; the total mole fraction percent of the three stabilising components when added together is necessarily 100 percent.

TABLE I

| Contour | Tertiary Butanol Mole fraction % | 1-Nitropropane Mole fraction % | Nitromethane Mole fraction % |
| --- | --- | --- | --- |
| K | 3 to 87 | 3 to 50 | 3 to 84 |
| L | 20 to 83 | 3 to 40 | 7 to 77 |
| M | 35 to 80 | 3 to 34 | 10 to 62 |

Referring now to FIG. 2 the lines I, II and III of the triangle represent the mole fraction percent of each of the three components (I)t-butanol (II) nitromethane and (III)nitroethane. Contour A encompasses an area representing the broadest range of the mole fraction percent of the three components which are within the scope of the invention. Contour B encompasses an area representing a preferred range of mole fractions percent of the three components.

Contour C encompasses an area representing an especially preferred range of mole fractions percent of the three components. The ranges represented by the contours are given for convenience in the following Table II. The total mole fraction percent of the three stabilising components when added together is necessarily 100 percent.

TABLE II

| Contour | Mole Fraction % Tertiary Butanol | Mole Fraction % Nitromethane | Mole Fraction % Nitroethane |
| --- | --- | --- | --- |
| A | 15 to 90 | 1 to 84 | 1 to 74 |
| B | 35 to 90 | 1 to 59 | 1 to 56 |
| C | 45 to 90 | 1 to 54 | 1 to 49 |

One outstanding effect of the present invention is that 1,1,1-trichloroethane stabilised with a mixture of the three components in the mole fraction percent ranges within the area encompassed by Contour K or Contour A is highly effective against the corrosive effect of light metals, especially aluminium. For greatest effectiveness of the mixtures of this respect we prefer mixtures within the area encompassed by Contour L or Contour B and especially mixtures within the area encompassed by Contour M or Contour C. The effectiveness of the stabiliser against the corrosive effect of light metals can be determined by the colour developed (in Hazen units) in the presence of aluminium, as more particularly described hereinafter.

Contour K, L and M shown in the triangular diagram of FIG. 1 the figures quoted in Table I and Contours A, B and C shown in the triangular diagram of FIG. 2 and the figures quoted in Table II are based on results obtained using stabilised 1,1,1-trichloroethane in which the total molar concentration of the three components was 0.8 moles/liter. However these mole fractions percent ranges apply to 1,1,1-trichloroethane having any total molar concentration of the components, i.e. the percentage ranges are independent of the total molar concentration of the stabilizing components.

The actual molar concentrations chosen of the stabilisers within the defined ranges will depend on several factors, including for example, cost and availability of the individual stabilisers and the degree of stability required in the stabilised solvent. The latter may depend on the use for which the solvent is required, e.g. the degreasing procedure to be utilised, for example whether a cold cleaning or a vapour cleaning technique is to be used. Even with a small fraction of one mole per liter total concentration of the three stabilising components, the improved results of the present invention are obtained. Obviously a large excess of stabilisers over what is required to confer the desired degree of stability to the solvent is unnecessary and wasteful. Generally however, it is usual to employ a total of from 0.3 to 1.5 moles per liter of the stabilising components; preferably there is employed a total of from 0.6 to 1.2 moles per liter of the components.

The stabilisation of 1,1,1-trichloroethane against corrosive attack by light metals, especially aluminium, is highly desirable but is not the only requirement for adequate stabilisation of 1,1,1-trichloroethane. Thus for example in typical vapour degreasing processes using stabilised 1,1,1-trichloro ethane, the liquid composition is heated to boiling and the resulting vapour is condensed and returned to the boiling liquid. Such degreasing processes are often unsatisfactory in that stabilisation of the solvent may be adequate when the solvent is in the liquid phase but not adequate when the solvent is in the vapour phase (or the condensate therefrom); alternatively stabilisation may be satisfactory when the solvent is in the vapour phase but not adequate when the solvent is in the liquid phase. However another outstanding effect of the present invention is that there is adequate distribution of the stabilising components in both the liquid and vapour phases such that the solvent is stabilised in both phases. As a result of this, the desired stabilising effects are maintained over a very considerable period of time of use of the solvent in vapour degreasing operations.

In addition to the considerations referred to hereinbefore, there are at the present time other demands on a stabilising system for 1,1,1-trichloroethane. One of these is concerned with the occurrence of a violent reaction of the solvent with, inter alia, flaked aluminium. The invention affords the further advantage that with the present stabilised solvent such violent reactions do not occur.

The stabilised 1,1,1-trichloroethane of the invention may if desired contain additional stabilisers for 1,1,1-trichloroethane, for example, an epoxide (eg 1,2-butylene oxide), another alkanol (eg tertiary amyl alcohol or isobutanol), an alkoxy alcohol (eg 2-methoxyethanol), and an N-alkyl-substituted pyrrole. As stated hereinbefore the actual total molar concentration of the stabilising components in the solvent is not critical providing the relative proportions of the components in the mixture is as defined herein. The solution may if desired be in the form of a concentrate for dilution with unstabilised or inadequately stabilised 1,1,1-trichloroethane, and such a concentrate is provided according to a further feature of the invention. By adding such a concentrate to pure solvent or solvent depleted in stabilising components, there can be obtained 1,1,1-trichloroethane containing the desired small amounts of said components which can then be used directly, e.g. for cleaning metal. The concentrate may contain additional components as aforesaid.

The present invention therefore provides 1,1,1-trichloroethane stabilised by a mixture comprising tertiary butanol, nitromethane and nitropropane or nitroethane in the mole fractions percent as hereinbefore described, which solvent may optionally contain additional stabilisers.

The invention provides as a preferred embodiment a method of inhibiting decomposition of 1,1,1-trichloroethane due to the presence of metals which comprising incorporating in said solvent a stabilising mixture of tertiary butanol nitromethane and nitropropane or nitroethane as hereinbefore described. The invention also includes a method of degreasing metal and other articles which comprise bringing them into contact with 1,1,1-trichloroethane or the vapour thereof containing a stabilising mixture of tertiary butanol, nitromethane and nitropropane or nitroethane as hereinbefore described.

The following Examples illustrate the invention.

EXAMPLE 1

Solvent compositions were made up consisting of 1,1,1-trichloroethane containing specific molar fractions percent of tertiary butanol, nitromethane and 1-nitropropane. These are defined in Table III and correspond to points F,G,H,I and J in FIG. 1 of the accompanying drawings. The total molar concentration of the three components in the solvent compositions was 0.8 mole per liter. The concentration in moles per liter and the percentage by weight of each individual component were calculated.

The stabilised compositions were subjected to an accelerated stability test. This test involved taking aluminium particles of approximate size 5×10.×0.15 mm, degreasing them with boiling trichloroethylene, pickling them with nitric acid, rinsing them with water and drying. 5 g of the dry particles were added to 200 mls of 1,1,1-trichloroethane containing the stabilising mixture under test. The mixture was vigorously agitated by stirring at a speed of 8600 rpm for 10 minutes and then was allowed to stand for 30 minutes. The mixture of solvent composition and particles was filtered and the filtrate was analysed to determine the colour developed (in Hazen units) on a Lovibond 1000 Nesslerizer, against a standard which was pure (unstabilised) 1,1,1-trichloroethane. The test was carried out in duplicate on each composition under test and the value shown in Table III is the average of the results of the two tests. (Figures for Mole per liter and % by weight are quoted only to the first place of decimals).

By way of comparison a solvent composition was made up comprising 1,1,1-trichloroethane containing a mixture of stabilising components wherein the mole fractions percent of the stabilising components were outside the scope of the invention. The total molar concentration of the components was again 0.8 mole per liter. The composition is defined in Table III and corresponds to point N in FIG. 1 of the drawings. The results are shown in Table III.

By way of comparison also, 1,1,1-trichloroethane containing a single stabilising component was submitted to the same test. The results are shown in Table III.

EXAMPLE 2

A glass flask was connected at its upper extremity by a glass side arm with a simple distillation column surmounted by a water-cooled condenser. The distillation column was provided near its bottom end with a glass U-tube connected with the flask to permit return of condensed vapours (condensate) from the column to the flask.

Into the flask were placed 80 mls 1,1,1-trichloroethane containing 50 mole fraction percent tertiary butanol, 35 mole fraction percent nitromethane and 15 mole fraction percent 1-nitropropane. The total molar concentration of the three stabilising components was 0.8 mole per liter. The contents of the flask were boiled, and when steady-state conditions had been established (after 3 hours) the stabiliser content of the solution in the flask and of the condensate from the column were determined. Thereafter, a sample of the original solution, the condensate from the column, and the solution in the flask were subjected to the stability test against aluminium described in Example 1. The results are shown in Table IV.

By way of comparison 80 mls of 1,1,1-trichloroethane containing separately tertiary butanol, nitromethane and 1-nitropropane in a molar concentration of 0.8 mole per liter were submitted to the same test. The results are shown in Table IV.

EXAMPLE 3

A solvent composition was made up consisting of 1,1,1-trichloroethane containing the following mixture of stabilising components in the molar concentrations shown:

| tertiary butanol | 0.35 Mole per liter |
|---|---|
| nitromethane | 0.24 Mole per liter |
| 1-nitropropane | 0.10 Mole per liter |
| isobutanol | 0.14 Mole per liter |
| 1.2-butene oxide | 0.09 Mole per liter |
| N—methyl pyrrole | 0.01 Mole per liter |

The mole fractions percent of tertiary butanol, nitromethane and 1-nitropropane were 51, 35 and 14, respectively, (total 100%), The total molar concentration of these three stabilising components was 0.69 mole per liter.

The percentages by weight of the stabilising components were:

| tertiary butanol | 2 |
|---|---|
| nitromethane | 1.1 |
| 1-nitropropane | 0.7 |
| isobutanol | 0.8 |
| 1,2-butene oxide | 0.5 |
| N—methyl pyrrole | 0.02 |

The solvent composition was subjected to very vigorous tests for determining the possibility of occurrence of violent reaction in the presence of inter alia flaked aluminium.

EXPERIMENT 1

100 mls of the solvent composition were mixed with 100 mls of toluene and 18 g of flaked aluminium, (maximum diameter 1 mm) and 0.7 g of aluminium chloride was added to the mixture. The total mixture was placed in a 500 ml round-bottomed glass flask which was surmounted by a water-cooled condenser which itself was surmounted by a drying-tube containing calcium chloride. The flask was immersed in an oil bath to a depth at which the fluid level in the flask was about 2 cms below the surface of the oil bath. The oil bath was heated and the contents of the flask were maintained at 114° C. (the liquid mixture in the flask being under reflux conditions) for 18 hours.

EXPERIMENT 2

In a similar experiment, 100 mls of the solvent composition were mixed with 100 mls of toluene and refluxed with 18 g of flaked aluminium and 1 g of zinc stearate.

EXPERIMENT 3

In a similar experiment a mixture of the solvent composition and toluene were refluxed with 18 g of flaked aluminium, 0.7 g of aluminium chloride and 10 ml of oleic acid.

EXPERIMENT 4

The solvent composition was separated into three equal volume fractions by simple distillation. 100 mls of each of the three fractions was mixed separately with an equal volume of toluene and flaked aluminium (18 g) and aluminium chloride (0.7 g) were added to the mixture. Each mixture was heated under reflux conditions in the manner described in Experiment 1.

RESULTS

No violent exothermic reaction occurred in any of the experiments.

EXAMPLE 4

A solvent composition (54 liters) as defined in Example 3 was prepared and placed in the cleaning compartment of a standard degreasing plant constructed of galvanised steel. The length, width and depth of the cleaning compartment were 60 cms, 35 cms and 52 cms, respectively. The apparatus was electrically heated to boil the solvent composition and the vapour was condensed by water-cooled copper coils and returned to the cleaning compartment. No provision was made to remove water from the condensed vapour. 200 mls/day of an aqueous cutting oil were added to the cleaning compartment.

The presence of water in the solvent composition increases the attack by corrosion on the plant and increases the likelihood of decomposition of the solvent. This is well known. Surprisingly, however, it was observed that the contents of the degreasing bath were heated continuously under reflux conditions for a period of 646 hours before the acid acceptance value of the solvent composition fell to zero. The acid acceptance value of a composition represents the capability of the composition to accept hydrogen chloride developed by degradation of 1,1,1-trichloroethane. The solvent remained clear and colourless for most of the test.

The test was repeated but this time with a separator being provided to remove water from the condensed vapor. Better results were achieved in that the contents of the cleaning tank were heated continuously for a period of 1609 hours before the acid acceptance value of the solvent composition fell to zero.

The above procedures were repeated with the solvent composition as described hereinbefore except that the composition contained 2-nitropropane instead of 1-nitropropane. In the absence of a water separator the contents were heated under reflux for 622 hours before the acid acceptance value of the solvent composition fell to zero. In the presence of a water separator the relevant period was 1126 hours.

EXAMPLE 5

A solvent composition was prepared as described in Example 3 but using 2-nitropropane instead of 1-nitropropane. 12 liters of the composition were distributed in the compartments of a standard two-compartment degreasing plant of which the length, width and depth of the compartments were 25 cms, 15 cms, and 30 cms, respectively. The heated degreasing plant was provided with a water-separator for removing water from condensed vapours, and was made of stainless steel. Approximately 400 mls/day of water were found to enter the plant. A galvanised mild-steel panel was suspended half immersed in the boiling solvent in the rinse compartment of the plant and protected by baffles from impingement of water bubbles. The degreasing plant was operated for a period of 1230 hours after which time the surface of the test panel was hardly affected either above or below the liquid solvent level, and there was little evidence of any corrosive attack on the degreasing plant.

EXAMPLE 6

A solvent composition (12 liters) was made up as in Example 3. The composition was distributed in the compartments of a standard two-compartment degreasing plant constructed of stainless steel. The length, width and depth of the compartments were 20 cms, 20 cms and 15 cms respectively. 50 g of aluminium swarf was placed in both the cleaning and rinsing compartments.

After the degreasing plant had been running for 600 hours (liquors at the boil) the plant was shut down and the total chloride ion deposited on the plant walls, in the solvent and deposited on the swarf was determined. The analysis showed that a total of only 3.46 mg of chloride ion had been liberated by degradation of 1,1,1-trichloroethane.

EXAMPLE 7

Solvent compositions were made up consisting of 1,1,1-trichloroethane containing specific molar fractions percent of the three stabilising components tertiary butanol, nitromethane and nitroethane. The total molar concentration of the three components in the solvent compositions was 0.8 mole per liter. The concentration in moles per liter and the percentage by weight of each component were calculated. The compositions are defined in Table V and corresponded to points D, E and F in FIG. 2 of the accompanying drawings.

The stabilised compositions were subjected to the accelerated stability test described in Example 1. The test was carried out in duplicate and the value shown in Table V is the average of the two tests. (Figures for Mole per liter and % by weight are to the first place of decimals).

By way of comparison a solvent composition was made up comprising 1,1,1-trichloroethane containing a mixture of the three stabilising components wherein the mole fractions percent of the three stabilising components were outside the scope of the invention. The total molar concentration of the components was again 0.8 mole per liter. The composition corresponded to point G in FIG. 2 of the drawings. The results are shown in Table V.

By way of comparison also, 1,1,1-trichloroethane containing a single stabilising component was submitted to the same test. The results are shown in Table V.

EXAMPLE 8

The apparatus described in Example 2 was assembled.

Into the flask were placed 80 ml 1,1,1-trichloroethane containing 50 mole fraction percent tertiary butanol, 35 mole fraction percent nitromethane and 15 mole fraction percent nitroethane. The total molar concentration of the three stabilising components was 0.8 mole per liter. The contents of the flask were boiled and when steady-state conditions had been established (after 3 hours) the stabiliser content of the solution in the flask and of the condensate from the column were determined. Thereafter a sample of the original solution, the condensate from the column and the solution in the flask were subjected to the stability test against aluminium as described in Example 1. The results were as shown in Table VI.

By way of comparison 80 mls 1,1,1-trichloroethane containing (separately) the same molar concentration (0.8 mole per liter) of tertiary butanol, nitromethane and nitroethane were submitted to the same test. The results are shown in Table VI.

EXAMPLE 9

A solvent composition was made up consisting of 1,1,1-trichloroethane containing the following mixture of stabilising components in the molar concentrations shown:

| | |
|---|---|
| tertiary butanol | 0.35 Mole per liter |
| nitromethane | 0.24 Mole per liter |
| nitroethane | 0.12 Mole per liter |
| isobutanol | 0.14 Mole per liter |
| 1.2-butene oxide | 0.09 Mole per liter |
| N—methyl pyrrole | 0.01 Mole per liter |

The mole fractions percent of tertiary butanol, nitromethane and nitroethane were 49, 34 and 17, respectively, (total 100%). The total molar concentration of these three stabilising components was 0.71 mole per liter.

The percentages by weight of the stabilising components were:

| | |
|---|---|
| tertiary butanol | 2 |
| nitromethane | 1.1 |
| nitroethane | 0.7 |
| isobutanol | 0.8 |
| 1,2-butene oxide | 0.5 |
| N—methyl pyrrole | 0.02 |

The solvent composition was subjected to very vigorous tests for determining the possibility of occurrence of violent reaction in the presence of inter alia flaked aluminium.

EXPERIMENT 1

100 ml of the solvent composition were mixed with 100 ml of toluene and 18 g of flaked aluminium (maximum diameter 1 mm) and 0.7 g of aluminium chloride was added to the mixture. The total mixture was placed in a 500 ml round-bottomed glass flask which was surmounted by a water-cooled condenser, which itself was surmounted by a drying-tube containing calcium chloride. The flask was immersed in an oil bath to a depth at which the fluid level in the flask was about 2 cms below the surface of the oil bath. The oil bath was heated and the contents of the flask were maintained at 114° C. (the liquid mixture in the flask being under reflux conditions) for 18 hours.

EXPERIMENT 2

In a second experiment 100 ml of the solvent composition were mixed with 100 ml of toluene and refluxed with 18 g flaked aluminium, 0.7 g of aluminium chloride and 1 g of zinc stearate.

EXPERIMENT 3

In a third experiment the solvent composition and toluene were refluxed with 18 g of flaked aluminium, 0.7 g of aluminium chloride and 10 ml of oleic acid.

EXPERIMENT 4

The solvent composition was separated into three equal fractions by simple distillation. 100 ml of each of the three fractions was mixed separately with an equal volume of toluene. Flaked aluminium (18 g) and aluminium chloride (0.7 g) were added to the mixtures. Each mixture was heated under reflux conditions in the manner described in Experiment 1.

RESULTS

No violent exothermic reaction occurred in any of the experiments.

TABLE III

| Mixture (see FIG. 1) | Tertiary Butanol Mole Fraction % | Mole per liter | % w/w | Nitromethane Mole Fraction % | Mole per liter | % w/w | 1-Nitropropane Mole Fraction % | Mole per liter | % w/w | Colour (Hazen Units) |
|---|---|---|---|---|---|---|---|---|---|---|
| F | 10 | 0.1 | 0.5 | 60 | 0.5 | 2.2 | 30 | 0.2 | 1.5 | 600 |
| G | 30 | 0.2 | 1.3 | 60 | 0.5 | 2.2 | 10 | 0.1 | 0.5 | 300 |
| H | 46.5 | 0.4 | 2.1 | 25 | 0.2 | 0.9 | 28.5 | 0.2 | 1.5 | 20 |
| I | 52.5 | 0.4 | 2.4 | 35 | 0.3 | 1.3 | 12.5 | 0.1 | 0.7 | 15 |
| J | 75 | 0.6 | 3.4 | 19 | 0.15 | 0.7 | 6 | 0.05 | 0.3 | 65 |
| COMPARITIVE EXAMPLES | | | | | | | | | | |
| N | 22.5 | 0.2 | 1.0 | 15 | 0.1 | 0.6 | 62.5 | 0.5 | 3.4 | 5500 |
| I | 0.8 mole per liter tertiary butanol | | | | | | | | | 5500 |
| II | 0.8 mole per liter nitromethane | | | | | | | | | 1000 |
| III | 0.8 mole per liter 1-nitropropane or 2-nitropropane | | | | | | | | | 5000 |
| IV | 0.8 mole per liter nitroethane | | | | | | | | | 3000 |

TABLE IV

| Stabiliser mixture | ORIGINAL mole per liter | % w/w | Colour (Hazen Unit) | DISTILLATE Mole per liter | % w/w | Colour (Hazen Units) | FLASK Mole per liter | % w/w | Colour (Hazen Units) |
|---|---|---|---|---|---|---|---|---|---|
| Tertiary Butanol | 0.4 | 2.4 | | 0.5 | 2.6 | | 0.3 | 1.8 | |
| Nitromethane | 0.3 | 1.4 | 20 | 0.3 | 1.4 | 15 | 0.3 | 1.2 | 275 |
| 1-Nitropropane | 0.1 | 0.8 | | 0.1 | 0.6 | | 0.2 | 1.0 | |
| COMPARITIVE EXAMPLES | | | | | | | | | |
| Tertiary Butanol | 0.8 | 4.5 | 5500 | 1.0 | 5.6 | 1300 | 0.5 | 2.5 | 10000 |
| Nitromethane | 0.8 | 3.7 | 1000 | 1.0 | 4.5 | 320 | 0.6 | 0.6 | 10000 |
| Nitropropane | 0.8 | 5.4 | 10000 | 0.3 | 1.9 | 10000 | 1.3 | 1.3 | 10000 |

TABLE V

| Point | Tertiary Butanol Mole Fraction % | Mole per liter | % w/w | Nitromethane Mole Fraction % | Mole per liter | % w/w | Nitroethane Mole Fraction % | Mole per liter | % w/w | Colour (Hazen Units) |
|---|---|---|---|---|---|---|---|---|---|---|
| D | 30 | 0.25 | 1.3 | 50 | 0.4 | 1.8 | 20 | 0.15 | 0.9 | 450 |
| E | 40 | 0.35 | 2.0 | 30 | 0.25 | 1.1 | 30 | 0.2 | 1.4 | 195 |
| F | 60 | 0.5 | 2.7 | 20 | 0.15 | 0.7 | 20 | 0.15 | 0.9 | 10 |
| COMPARISON EXAMPLES | | | | | | | | | | |
| G | 10 | 0.1 | 0.5 | 20 | 0.15 | 0.7 | 70 | 0.55 | 3.2 | 3600 |
| V | 0.8 mole per liter tertiary butanol | | | | | | | | | 5500 |
| VI | 0.8 mole per liter nitromethane | | | | | | | | | 1000 |
| VII | 0.8 mole per liter nitroethane | | | | | | | | | 3000 |
| VIII | 0.8 mole per liter nitropropane | | | | | | | | | 5000 |

TABLE VI

| Stabiliser | ORIGINAL Mole per liter | % w/w | Colour (Hazen Unit) | DISTILLATE Mole per liter | % w/w | Colour (Hazen Units) | FLASK Mole per liter | % w/w | Colour (Hazen Units) |
|---|---|---|---|---|---|---|---|---|---|
| Tertiary Butanol | 0.4 | 2.4 | | 0.5 | 2.6 | | 0.3 | 1.8 | |

TABLE VI-continued

| Stabiliser | ORIGINAL | | | DISTILLATE | | | FLASK | | |
|---|---|---|---|---|---|---|---|---|---|
| | Mole per liter | % w/w | Colour (Hazen Unit) | Mole per liter | % w/w | Colour (Hazen Units) | Mole per liter | % w/w | Colour (Hazen Units) |
| | | | 225 | | | 15 | | | 125 |
| Nitromethane | 0.3 | 1.4 | | 0.3 | 1.4 | | 0.3 | 1.2 | |
| 1-Nitroethane | 0.1 | 0.6 | | 0.1 | 0.4 | | 0.1 | 0.7 | |
| COMPARISON EXAMPLES | | | | | | | | | |
| Tertiary Butanol | 0.8 | 4.5 | 10,000 | 1.0 | 5.6 | 800 | 0.5 | 2.5 | 10000 |
| Nitromethane | 0.8 | 3.7 | 520 | 1.0 | 4.5 | 85 | 0.6 | 0.6 | 10000 |
| Nitroethane | 0.8 | 4.5 | 1750 | 0.7 | 3.9 | 10000 | 1.0 | 5.6 | 1100 |

We claim:

1. A mixture of stabilising components for the stabilisation of 1,1,1-trichloroethane, characterised in that the mixture comprises (i) tertiary butanol, (ii) nitromethane and (iii) 1- or 2-nitropropane or nitroethane wherein the mole fractions percent of the stabilising components are within the ranges encompassed by Contour K in FIG. 1 of the drawings or by Contour A in FIG. 2 of the drawings.

2. A method of inhibiting decomposition of 1,1,1-trichloroethane by metals which comprises incorporating a mixture of stabilising components in the 1,1,1-trichloroethane, characterised in that the mixture of stabilising components is as claimed in claim 1.

3. A solvent composition comprising 1,1,1-trichloroethane having a stabilising amount of a mixture of stabilising components dissolved therein, characterized in that the mixture of stabilizing components comprises (i) tertiary butanol, (ii) nitromethane and (iii) 1- or 2-nitropropane or nitroethane in which the mole fractions percent of the stabilizing components are within the ranges encompassed by Contour K in FIG. 1 of the accompanying drawings or by Contour A in FIG. 2 of the accompanying drawings.

4. A solvent composition as claimed in claim 3, characterized in that component (iii) of the mixture of stabilising components is 1- or 2-nitropropane and the mole fractions percent of the stabilising components are within the ranges encompassed by Contour L in FIG. 1 of the accompanying drawings.

5. A solvent composition as claimed in claim 4, characterised in that the mole fractions percent of the stabilising components are within the ranges encompassed by Contour M in FIG. 1 of the accompanying drawings.

6. A solvent composition as claimed in claim 3, characterized in that component (iii) of the mixture of stabilising components is nitroethane and the mole fractions percent of the stabilising components are within the ranges encompassed by Countour B in FIG. 2 of the accompanying drawings.

7. A solvent composition as claimed in claim 6, characterized in that the mole fractions percent of the stabilising components are within the ranges encompassed by Contour C in FIG. 2 of the accompanying drawings.

8. A solvent composition as claimed in claim 3, characterized in that the stabilising amount of the mixture of stabilising components is from 0.3 to 1.5 mole per liter.

9. A solvent composition as claimed in claim 8, characterised in that the stabilising amount of the mixture is from 0.6 to 1.2 mole per liter.

10. A solvent composition for dilution with 1,1,1-trichloroethane to provide a solvent composition as claimed in claim 3, characterized in that the composition is in the form of a concentrate containing an excess of the mixture of stabilising components over the stabilising amount.

11. A solvent composition as claimed in claim 3 wherein the stabilising component (iii) is nitropropane together with an additional stabilising component which is nitroethane.

12. A solvent composition as claimed in claim 3 wherein the stabilising component is nitroethane together with an additional stabilising component which is 1- or 2-nitropropane.

13. A method of cleaning metal and other articles which comprises contacting the articles with a solvent composition or the vapour thereof, characterised in that the solvent composition is as claimed in claim 3.

* * * * *